(12) United States Patent
Kurani et al.

(10) Patent No.: US 9,776,888 B1
(45) Date of Patent: Oct. 3, 2017

(54) WATER MONITORING DEVICE AND METHOD

(71) Applicant: DATA2O, San Francisco, CA (US)

(72) Inventors: Ravi Kurani, San Francisco, CA (US); Andrew Redfern, San Francisco, CA (US); Daniel Proterra, San Francisco, CA (US); Jakob Grano, San Francisco, CA (US); Michael Clayton, Berkeley, CA (US)

(73) Assignee: DATA2O, San Francisco, CA (US)

( * ) Notice: Subject to any disclaimer, the term of this patent is extended or adjusted under 35 U.S.C. 154(b) by 0 days.

(21) Appl. No.: 14/988,554

(22) Filed: Jan. 5, 2016

Related U.S. Application Data

(60) Provisional application No. 62/099,684, filed on Jan. 5, 2015, provisional application No. 62/274,737, filed on Jan. 4, 2016.

(51) Int. Cl.
| | | |
|---|---|---|
| *C02F 1/00* | (2006.01) | |
| *G08B 5/22* | (2006.01) | |
| *G08B 21/20* | (2006.01) | |
| *C02F 1/66* | (2006.01) | |
| *G01N 31/22* | (2006.01) | |
| *C02F 103/42* | (2006.01) | |

(52) U.S. Cl.
CPC ............. *C02F 1/008* (2013.01); *C02F 1/66* (2013.01); *G01N 31/22* (2013.01); *G01N 31/221* (2013.01); *G08B 5/22* (2013.01); *G08B 21/20* (2013.01); *C02F 2103/42* (2013.01); *C02F 2209/006* (2013.01); *C02F 2209/04* (2013.01); *C02F 2209/06* (2013.01); *C02F 2209/07* (2013.01); *C02F 2209/08* (2013.01)

(58) Field of Classification Search
None
See application file for complete search history.

(56) References Cited

U.S. PATENT DOCUMENTS

| | | | |
|---|---|---|---|
| 6,625,824 B1* | 9/2003 | Lutz | E04H 4/12 137/625.21 |
| 2005/0276724 A1* | 12/2005 | Bremauer | B01F 15/0217 422/29 |
| 2006/0241874 A1* | 10/2006 | Carter | C02F 1/008 702/50 |
| 2013/0210156 A1* | 8/2013 | Wooley | A61B 5/14539 436/63 |
| 2016/0052798 A1* | 2/2016 | Downs | C02F 1/008 210/742 |

* cited by examiner

*Primary Examiner* — Leon-Viet Nguyen
(74) *Attorney, Agent, or Firm* — Staniford Tomita LLP

(57) ABSTRACT

A water monitoring device monitors and maintains swimming pool chemistry. The device includes sensors that detect water chemistry. The water monitoring device can communicate with computers and servers. This system can be used to determine if corrections to the water chemistry are required to maintain water sanitation. The device can monitor: pH, air temperature, water temperature, free chlorine levels, oxidation reduction potential, alkalinity, oxygen demand, water movement and velocity, and electrical conductivity.

18 Claims, 15 Drawing Sheets

WATER MONITORING DEVICE AND METHOD

CROSS REFERENCE TO RELATED APPLICATIONS

This patent application claims priority to U.S. Provisional Patent Application No. 62/099,684, "WATER MONITORING DEVICE AND METHOD" filed Jan. 5, 2015 and U.S. Provisional Patent Application No. 62/274,737, "WATER MONITORING DEVICE AND METHOD" filed Jan. 4, 2016, which are hereby incorporated by reference in their entirety.

BACKGROUND

Pool owners often manage their own swimming pool chemistry and equipment. There are 14.4 million residential pools and spas in the United States with 85% of pool owners managing their own pool. Managing chemistry is the largest problem for 80% of pool owners since managing a pool is confusing and time consuming, and purchasing pool products is complicated. Pool owners may spend upwards of 4-6 hours on chemical management and skimming pool water. With current pool management kits, owners often manage their pool incorrectly, resulting in a cumulative $960 extra spent on pool mismanagement, 176 billion gallons of water used and misused, and 20% more energy wasted on running dirty pools. Individually, pool and spa owners spend upwards of $120/month on chemicals and, on average, their pool goes 'green' meaning, it grows algae or gets cloudy usually caused by a pH imbalance once a season. This algae growth and its prevention are not well understood by end-users. Users spend extra money on toxic chemicals to try to "reset" their water chemistry, energy costs because dirty water takes more energy to circulate, repairing equipment malfunctions due to dirty water, and water costs due to dumping and replacing dirty water. What is needed is a monitoring system that will help owners properly maintain their pools and spas so that they are always in proper pH balance to save money, conserve water and prevent unnecessary maintenance.

SUMMARY OF THE INVENTION

A water monitoring device monitors and maintains swimming pool chemistry. The device includes sensors that detect water chemistry that can communicate with a pool computer and a server. The system can determine if corrections to the water chemistry are required to maintain water sanitation. The device can monitor: pH, air temperature, water temperature, free chlorine levels, oxidation reduction potential, alkalinity, oxygen demand, water movement and velocity, and electrical conductivity.

In an embodiment, as discussed above the device can include sensors, connectivity mechanisms, 'knowledge' of device's location, solar panels and/or battery, rounded disk-like design, mass-spring-dashpot system to aide in impact of sensor on the ground, water-proof housing, remote proprietary chemistry algorithms, mobile, web applications, and messaging capabilities. These processes can be performed by a processor that is coupled to sensors, transducers, a power supply and a memory. In an embodiment, the device may include sensors that can measure and provide proxy values for: pH levels, ambient air temperature, water temperature, free chlorine levels, ORP (oxidation reduction potential), alkalinity, oxygen demand (biological, chemical), etc. The system may also include an accelerometer that can be used to measure: fluctuations in water movement (or air movement), velocity at the water surface, electrical conductivity (total dissolved solids, salinity units, salinity, specific gravity), pressure at the water surface, pressure of water at the device submersion point, volume of water (as per user input).

In an embodiment, the device can include a connectivity mechanism which includes, but is not limited to RF transducers which can provide wireless communications with other devices through various protocols including: WiFi (IEEE 802.11, IEEE 802.11ac, IEEE 802.11n), Bluetooth and BLE (Bluetooth low energy), Electric Imp protocol, Zigbee, Z-Wave, Android OS, Apple iBeacon, PayPal proximity sensor, GPRS/GSM/3G/4G/Edge, etc. The transducers can provide a means for communications with other devices such as mobile phones, computers, other water sensor devices, etc.

In an embodiment, the device can include nodal mesh 'knowledge' of device's location. The location information can be useful in predicting the upcoming weather conditions. Water maintenance can be related to the ambient temperature. If warmer weather is predicted in the near future, the system can prepare the water by recommending an adjustment of the chemicals in the water prior to the increased temperatures. The warmer temperatures can result in more algae growth if the pool chemicals are not adjusted. The system can also recommend reducing the heating of the pools in areas where hot weather is predicted or increasing the heating of pools where cold weather is predicted to compensate for atmospheric thermal transfer conditions.

In an embodiment, the device can be powered by solar panels, which can maintain an electrical charge on a battery. During the day, the system can run off of solar power and when the solar panel is not collecting energy at night, the system can operate off of battery power.

In an embodiment, the design of the device may have a rounded conical or disc-like design. The product design may protrude into the water ending at a small, flat base. The device may also include an integrated LED-lighted ring that changes colors as both a customer-directed alert and entertainment or ornamental feature. The device may further include a rounded top edge. The device may have an integration of metal or metallic ring that covers the rounded top edge. In alternative embodiments, the design of the device may take on various shapes and sizes.

In an embodiment, the device can have an inlet of water near the base and reservoir—that includes a water or liquid circulation technology mechanism so new water is constantly being tested. This reservoir may hold liquid even when not submerged such that sensors are kept wet while out of water or other liquid.

In an embodiment, the device may include a mass-spring-dashpot system to aide in protecting the internal components and sensor from damage due to impact with the ground or from falling from a height. The housing of the device may also be impact resistant so that the structure will not break when dropped onto a hard surface such as a pool deck.

In an embodiment, the device may have liquid submersion functionality, including but not limited to submersion into pools, wells, waterways, rivers, spas, Jacuzzis, hot tubs, reservoirs of any kind, and applications related to agriculture, irrigation, aqueducts, drinking water, fracking, groundwater testing, city and municipal water wells and meters.

Although the water monitoring device has been illustrated as a device that floats on the surface of the water, with a portion submerged and a portion above the water line, in another embodiment, the device could be fully submerged at the bottom of a pool or other water source. Because radio frequency waves do not travel well through water, connective communication wires and/or tubes for the device can run up from a floor or wall(s) to a dry area outside of the body of water. The wires can provide electrical power as well as communications from the water monitoring device so that the device can function as described above.

In an alternative embodiment, the device could be placed on the outside of the pool, such as on a deck. One or more water sensors can be connected or in communication with the water monitoring device and these sensors can contact the water or be in close proximity to the water by hanging over the water surface.

Pools may have skimmers that can be installed outside the perimeter of the pool and function to remove floating debris from the pool. Water circulates from the pool to the skimmer and the debris can be trapped in baskets or filters that are held in the skimmers. The skimmer baskets or filters can be accessed by removing a lid of the skimmer that is adjacent to the edge of the pool. In an embodiment, the device can be placed in a lid such as a skimmer lid, where the lid is covering an access area to the inlet or outlet of the pool.

In another embodiment, the water monitoring device could be built into a heating, plumbing or filtration system when the water system structure is being constructed and later connected to a network. For example, the water monitoring device and/or sensors) could be placed inline with pool plumbing. In other embodiments, the water monitoring device and/or sensors) could be placed anywhere around the water system, as long as a portion of the sensor cluster comes in contact with the water. In an embodiment, the water monitoring device and/or sensor(s) could be attached onto a filter bank through a filter gauge installment.

In an embodiment, the water monitoring device and/or sensor(s) can be incorporated with other pool related products. For example, in an embodiment, the water monitoring device could include a music speaker set on an exposed above water portion with sensors attached to the bottom of a floating music device. The water monitoring device can include a Wi-Fi or Bluetooth receiver that can receive RF music signals and emit the music through the speaker set.

In an embodiment, the design could be attached to an automatic or human powered floating water top skimmer that can move across the surface of the pool cleaning the surface debris. In an embodiment, the design could be a replacement part for an existing automatic pool cleaner. For submerged pool cleaners, the water monitoring device can have communications waterproof insulated wires could be run through a hose or be attached to the pool cleaner hose with the opposite ends exiting the water.

In an embodiment, the device may include remote proprietary chemistry algorithms. These algorithms may include a pH and alkalinity buffer. The algorithm may make correlations to weather stations provided by governmental organizations, private organizations, or citizens through organizations like Smart Citizen. The algorithms may also process salt content, water hardness/softness, rate of evaporation, energy consumption as a function of chemical balances and electricity rates.

In an embodiment, the device includes application and messaging capabilities. For example, these capabilities may include communication via both inside application and through SMS, email, push notifications, wearable tech notifications, physical notifications through product indicators, etc. These communications may provide end users with actionable insight into their pool water chemistry and provide a sales and delivery platform of chemicals and/or solutions. For example, when more chemicals such as chlorine or acid are required, the system can transmit messages to the user indicating the chemical and quantity of the chemical needed. The user can respond to the messages by indicating that the specified chemicals will be added to the pool water at a predicted time period such as within 1 hour or any other time increment. If the system does not detect a change in water chemistry, it can transmit a reminder to the user soon after the predicted time period has elapsed. If the user does not add the requested chemicals, the system can update the quantity of requested chemicals as the conditions of the water change.

In an embodiment of the method of using the device, the device sends water data to a network, such as an analytics cloud. The network can then send tracking information and actionable data to a mobile device. The mobile device can then purchase pool maintenance products. The products can be shipped to the pool owner. The device can then instruct the owner on use of the pool maintenance products. In an embodiment, the device is set up once and will remain operational due to its solar panel power source and impact resistant housing.

In an embodiment, the device may include mobile, web applications and cloud-based database and associated UX/UI to facilitate pool, water, or liquid management. Data from the device can be transmitted and stored on a cloud server. This water and device data can then be stored for the water of the individual user or business. This data can provide a historical record of the water metrics and provide an analysis of the chemicals used by the system for any prior time period. Based upon the past history and/or the relationship between water and ambient conditions, the necessary chemicals can be predicted for future use.

Swimming pool water must maintain low levels of bacteria and viruses to prevent the spread of diseases and pathogens. Bacteria, algae and insect larvae can enter the pool if water is not properly sanitized. Pumps, mechanical filters, and disinfectants are often used to sanitize the water.

Chemical disinfectants, such as chlorine (usually as a hypochlorite salt, such as calcium hypochlorite) and bromine, are commonly used to kill pathogens. If not properly maintained, chemical sanitation can produce high levels of disinfection byproducts. Sanitized swimming pool water can theoretically appear green if iron or certain minerals (such as copper chloride) are in the water.

There are various types of chemicals that can be added to water. For example, water chlorination is the process of adding chlorine ($Cl_2$) or hypochlorite to water as a method of water purification to make it fit for human consumption as drinking water. In particular, chlorination is used to prevent the spread of waterborne diseases.

As a halogen, chlorine is a highly efficient disinfectant, and is added to public water supplies to kill disease-causing pathogens, such as bacteria, viruses, and protozoans, that commonly grow in water supply reservoirs, on the walls of water mains and in storage tanks. The microscopic agents of many diseases such as cholera, typhoid fever, and dysentery killed countless people annually before disinfection methods were employed routinely.

Chlorine is obtained from salt (NaCl). It is a gas at atmospheric pressures but liquefies under pressure. The liquefied gas is transported and used as such. As a strong oxidizing agent, chlorine kills via the oxidation of organic molecules. Chlorine and hydrolysis product hypochlorous acid are neutrally charged and therefore easily penetrate the negatively charged surface of pathogens. It is able to disintegrate the lipids that compose the cell wall and react with intracellular enzymes and proteins, making them nonfunctional. Microorganisms then either die or are no longer able to multiply.

Shock chlorination is a process used in many swimming pools, water wells, springs, and other water sources to reduce the bacterial and algal residue in the water. Shock chlorination is performed by mixing a large amount of hypochlorite into the water. The hypochlorite can be in the form of a powder or a liquid such as chlorine bleach (solution of sodium hypochlorite in water). Water that is being shock chlorinated should not be swum in or drunk until the sodium hypochlorite count in the water goes down to three parts per million (PPM) or less.

Salt water chlorination is a process that uses dissolved salt (2,500-6,000 ppm) as a store for the chlorination system. The chlorine generator (also known as salt cell, salt generator, salt chlorinator) uses electrolysis in the presence of dissolved salt (NaCl) to produce hypochlorous acid (HClO) and sodium hypochlorite (NaClO), which are the sanitizing agents already commonly used in swimming pools. As such, a saltwater pool is not actually chlorine-free; it simply utilizes a chlorine generator instead of direct addition of chlorine.

The presence of chlorine in traditional swimming pools can be described as a combination of free available chlorine (FAC) and combined available chlorine (CAC). While FAC is composed of the free chlorine ions that are available for sanitizing the water, the CAC includes chloramines, which are formed by the reaction of FAC with amines (introduced into the pool by human perspiration and urine). Chloramines are responsible for the "chlorine smell" of pools, as well as skin and eye irritation. These problems are the result of insufficient levels of free available chlorine, and indicate a pool that must be "shocked" by the addition of 5-10 times the normal amount of chlorine. In saltwater pools, however, the generator continuously produces free chlorine ions, eliminating the formation of CAC. Electrolysis burns off chloramines in the same manner as traditional shock (oxidizer). As with traditionally chlorinated pools, saltwater pools must be monitored in order to maintain proper water chemistry. Low chlorine levels can be caused by insufficient salt, higher-than-normal chlorine demand, low stabilizer, sun exposure, or mechanical issues with the generator. Salt count can be lowered due to splash-out, backwashing, and dilution via rainwater.

In different embodiments, the inventive system can be used to monitor the chemicals in any type of chemicals used to maintain the sanitation of the pool water. The system can be easily configured for chlorine or bromine or other water chemicals through the software or firmware set up of the device or in other embodiments an electrical switch on the device.

For example, the optimum pH level for a pool can be between about 7.4 and 7.6. If a pH reading is below 7.2 then the water is may be too acidic and if the pH reading is above 7.8, the water may be too alkaline. To keep bacterial, pathogens, and algae from growing in your water, the chlorine (sanitizer) level needs to be at a safe level for swimming. If the pH level is too low, the processor can recommend adding a pH or alkaline increaser such as backing soda can be added to the water. If the pH level is too high the processor can recommend adding a pH or alkaline decreaser such as syanuric acid. The amount of chemicals needed to change the pH level will depend upon the volume of the body of water. A smaller pool will need a smaller volume of chemicals to change the pH level than a larger pool.

In an embodiment, the depth sensor can detect an average depth of the pool based upon an average reading over a period of time when the water monitoring device 101 randomly moves across the entire surface of the pool. In an embodiment, the surface area of the pool can be determined from areal or satellite photographs of the pool such as Google maps or approximated by the general shape and dimensions of the pool. The volume of water can be calculated by multiplying the average depth times the surface area of the pool. In yet another embodiment, the system can initially estimate the volume of the pool based upon just the surface area of the pool as determined by the owner or calculated from areal or satellite photographs of the pool such as Google maps. The system can then estimate the volume based upon an average depth of a pool of 4.5 feet. However, the average depth of the pool may also be proportional to the size of the pool with larger pools typically having a larger average depth than smaller pools. The user can be offered up the surface area and may provide additional depth information. For example, the user may have to select a point where the deep end and possibly where shallow end is. From this information, the system can more accurately estimate the pool volume. The system can also perform learning tests to determine the pool volume. For example, the chlorine level can be measured and then 5 pounds of chlorine can be added. The chlorine level can be measured again and the increase in chlorine level will indicate the volume of the pool. In another example, if we originally assumed that the pool volume is 1,000,000 liters, and the user wants to increase the chlorine concentration by 1 ppm, then the system will prescribe 1 mg of chlorine. After the chlorine is added, the chlorine concentration can be remeasured to determine if the concentration actually increases by 1 ppm. If chlorine level increases more than 1 ppm, then we know that the pool was actually less than 1,000,000 liters. The actual volume of the pool can be determined by the chlorine level increase.

A smaller volume pool will have a larger ppm increase than a larger pool for the same quantity of chlorine. In other embodiments any other chemical concentration testing can be performed to determine the pool volume. With the pool volume accurately measured, the system can make more accurate chemical recommendations.

The processor recommendation can also be based upon the type of chemicals being used such as: granular chlorine, 1 inch or 3 inch tablets, sticks, etc. In an embodiment, the user may specify chemical preferences and the system may calculate a quantity of the chemicals based upon the chemical and/or pH level measurements, temperature and volume of pool water. Because the system can continuously monitor the chemical and pH levels, the system can update the chemical recommendations over time.

A chlorine test reading between 1.0 and 3.0 ppm is optimal. However, if bromine is used instead of chlorine as the sanitizer, then the bromine reading should be between 2.0 and 4.0 ppm. Again, the chlorine or bromine use can be set up as a user preference. Alkalinity should be between about 100 and 120 ppm. Cyanuric acid should be between about 20 and 30 ppm. If the chemical levels are too low, the system can recommend adding these chemicals based upon the ppm readings and the volume of the pool. The recommendations can provide sufficient chemicals to bring the chemicals to the optimum concentrations. However, if errors are made by the pool maintainer, the system will detect the errors and make adjustments to future chemical inputs. In addition to normal pool maintenance, the system can also schedule shock chemicals, and adjust the chemical recommendations afterwards. The system may also detect algae and make recommendations for specific volumes of algaecide based upon the detected quantities of algae. For example, the system can recommend adding 3 pounds of shock chemicals once a week at night and the recommend adding algaecide the next morning. The system may also recommend a sequence of steps to correct the chemical levels. For example, the system may recommend adjusting the alkalinity first. Once the alkalinity is determined to be in the proper range, the system can recommend adjusting the bromine or chlorine levels. After the alkalinity and bromine/chlorine levels are set, the system can recommend adjusting the pH level.

In different embodiments, different sensors can be used to determine the pH level. In an embodiment, a chamber is filled with water either through diffusion or via a peristaltic pump within the water monitoring device 101. Reagents are either mixed through a mixing chamber via a pump or via the diffusion. In alternative embodiments, the reagents can be added via a vacuum that is created through a pump. The reagents can diffuse in the water. In yet another embodiment, the reagents can be stored in a replaceable modular cartridge that is easily inserted and removed from the water monitoring device 101. The reagents react with the water to produce a coloring that indicates the pH level of the water. The photometer can include 3 RGB (1 red, 1 green and 1 blue) LEDs that can be used to allow the photometer to measure 'color' of the water after it has been mixed with reagents. The absorbance of the colored light is then compared to what we have limits for, and then the values are distilled to provide input to the consumer.

In an embodiment pH test paper strips can be used in an automated device to determine the pH level of the pool. For example, the test strip can be inserted into a tube filled with pool water and the sensor can include a camera that is used to identify the color of the test strip, the color processing used to recommend the chemical adjustment may be patentable. The color data may come back with RGB values or other color data output. An algorithm can then process this data and determine the pool chemistry based upon the light absorption values.

In another embodiment, the pH meter can be an electronic device coupled to a pH probe. A schematic diagram of the pH meter circuit is illustrated. Two power supplies provide power a high-input-impedance operational amplifier, such as a TL082. The pH probe of the meter is connected to the non-inverting input. The output voltage (V out), which is directly proportional to pH, is read with a voltmeter. The pH probe can produce about 59 millivolts (mV) per pH unit, and at pH 7 (neutral pH) the probe produces 0 volts. Acid pH can produce negative voltages. Basic pH can produce positive voltages. With the probe in pH 7.01 calibration buffer, the voltage output can be is +4.6 mV. With pH 4.00 calibration buffer, the output voltage can be 168.8 mV. This gives a range of 168.8-4.6=164.2 mV for 3.01 pH units, or 54.55 mV per pH unit. If, for example, I measure 100 mV, the pH is 100 mV/54.55 mV=1.83 pH units deviation from 7.01, so subtracting 1.83 from 7.01 provides a corrected measured pH of 5.18. Based upon the known pH levels, the system can then calculate the total chemicals to add based upon the total pool water volume and temperature.

In an embodiment, the pool chemicals can be stored in the water monitoring device 101 and released at the recommended rate. Since the chemicals are added through an automated device, the system can control the rate of flow of the chemicals to maintain the desired chemical balance. This constant chemical control would be better than periodic chemical adjustment because it would maintain a much better chemical balance rather than going through a cyclical chemical adjustment process.

While the above description contains many specificities, these should not be construed as limitations on the scope of any embodiment, but as exemplifications of various embodiments thereof. Many other ramifications and variations are possible within the teachings of the various embodiments. For example, the pool maintenance device may include more than one module. The device(s) may float freely, or be anchored, or attached to the pool. The modules may include audio functionality. The device modules may include additional functions, attachments related to pool maintenance and use.

DETAILED DESCRIPTION

The present invention monitors swimming pool and/or spa chemistry at all times and instructs owners what chemicals to add and when the pool chemicals are needed. In an embodiment, the inventive system may order the necessary pool chemicals as required. With the present invention, there is no need to guess at what pool products correspond to pool equipment, and no need to remember model numbers. The inventive device orders the correct pool products, giving pool and spa owners freedom and peace of mind.

In various embodiments, a device, and method of using the device, for monitoring swimming pool chemistry. The device and can comprise sensor(s), network connectivity, knowledge of device's location, circuitry, water proof housing, impact resistant housing, remote proprietary chemistry algorithms, mobile and web applications, messaging capability, and sales and delivery platforms. The device can also use integrated computer application(s) for water monitoring, water chemistry management, energy management, and water cleaning and chemistry correction. The sensor can detect water chemistry, and communicate with a network and mobile device(s) to manage pool maintenance. The sensor can have the ability to order water maintenance products, and instruct on water maintenance.

Figure 1:
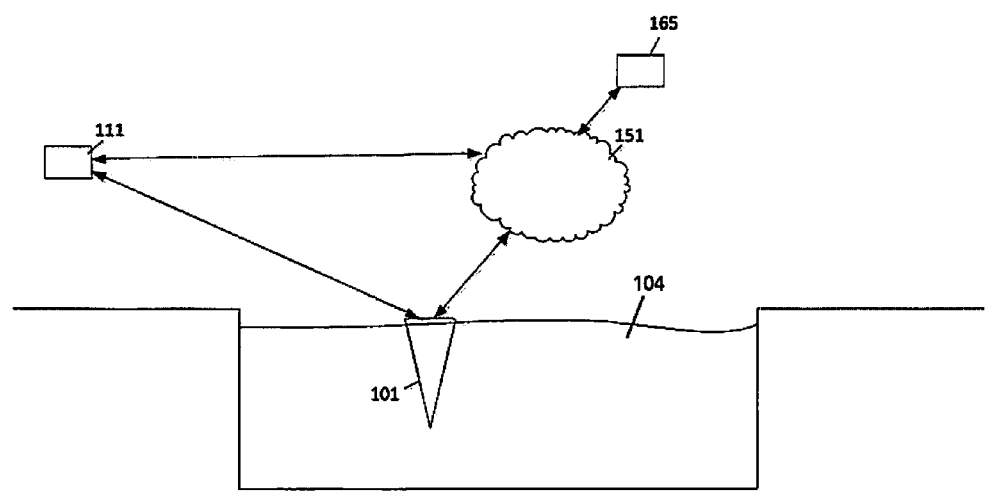
FIG. 1 illustrates a block diagram of an embodiment of water monitoring system components with a floating water monitoring unit.

The present invention is a device and method of using the device for monitoring and maintaining water. The device may contain an integrated computer application solution for water monitoring, water chemistry management, and water cleaning and chemistry correction. With reference to FIG. 1, a water monitoring system can include: a water monitor unit 101, a computing device 111, a network 151 and a server 165. The water monitoring unit 101 can be placed in a body of water 104 to monitor the water quality and chemicals within the water. In the illustrated embodiment, the body of water can be a pool or a spa and the water monitoring unit 101 can float and drift with the current within pool or spa. The water monitoring unit 101 can communicate with the computing device 111 which can be a computer, a tablet computer, a smart phone or any other suitable computing device. In an embodiment, the water monitoring unit 101 can communicate with the computing device 111 through a wireless network 151 such as a WIFI network.

The computing device 111 can run an application program, which can provide a user interface which can provide information to a pool owner or maintenance person. The system may also communicate with a remote server 165 which can provide app software downloads and updates to the computing device 111. The water monitoring unit 101 can also include a processor which runs software, which can be firmware, stored in read only memory coupled to the processor. In an embodiment, the firmware can be updated using any known update method.

Figure 2:
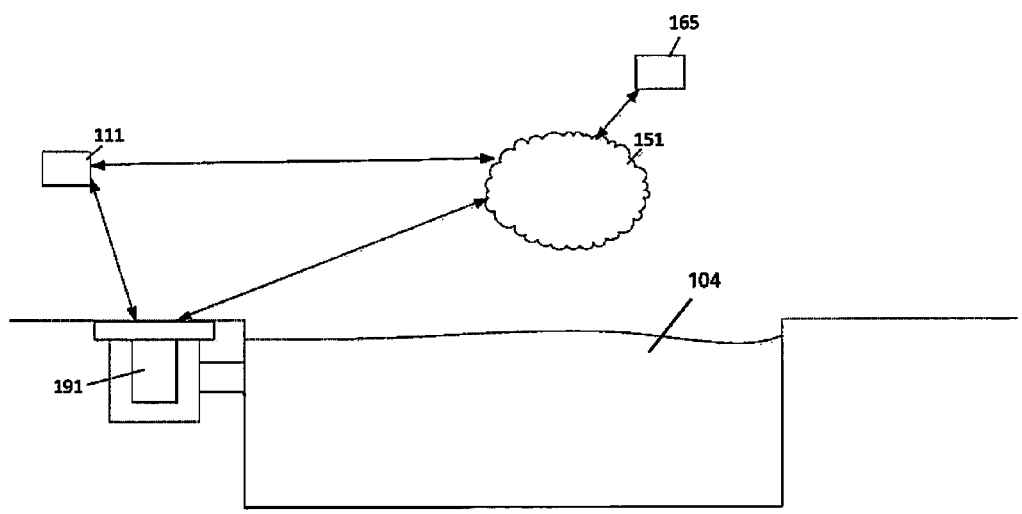
FIG. 2 illustrates a block diagram of an embodiment of water monitoring system components with an integrated monitoring unit.

With reference to FIG. 2, in an embodiment, the water monitoring unit 191 can be integrated into the pool 104. In the illustrated embodiment, the water monitoring unit 191 can be added to a pool skimmer. The pool skimmer can include a removable lid. In an embodiment, the water monitoring unit can be built into a replacement lid which can suspend the water monitoring unit 191 in a recessed volume of circulating pool or spa water.

Figure 4:
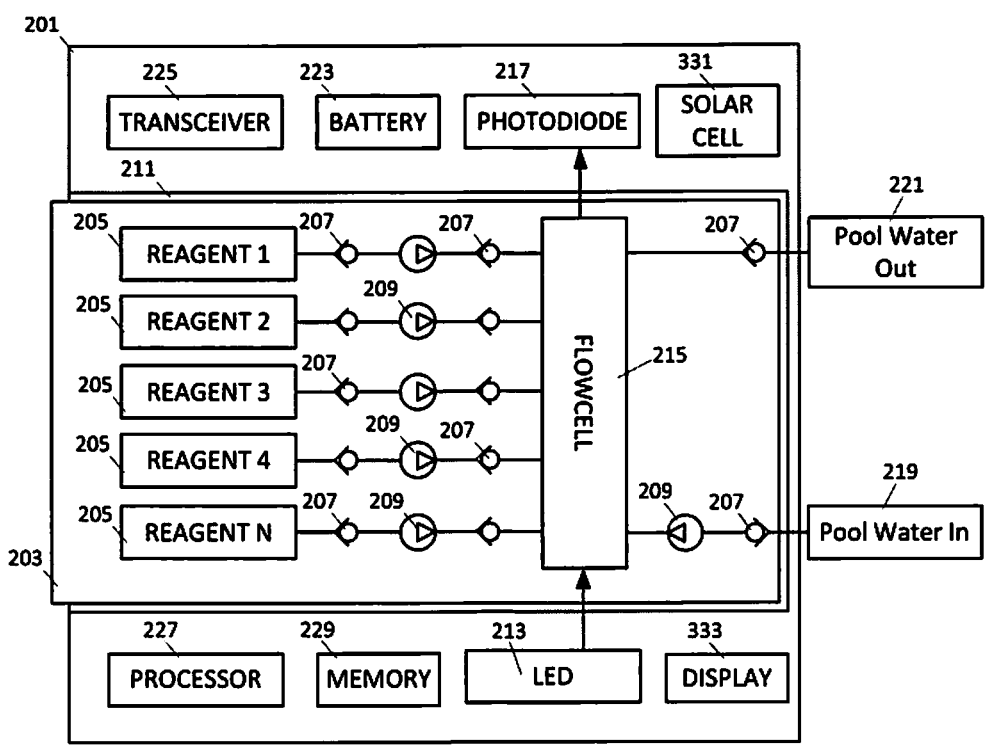
FIG. 4 illustrates a schematic diagram of an embodiment of the water monitoring unit.

With reference to FIG. 4, a block diagram of an embodiment of the water monitoring system 100 is illustrated. The water monitoring system 100 can include a water monitoring device 101 that can include a solar panel 111 that provides electricity to charge a battery 113 which can provide electricity to the other components of the water monitoring device 101 including a processor 115. The processor 115 can be communicate with various sensors including: a pH sensor 121, a temperature (ambient and water) sensor 123, a salinity sensor 125, a depth sensor 127, chemical sensors 129 which can include: Chlorine, Cyanuric Acid, Alkalinity, Bromine, etc. In other embodiments, the sensors may include used with the water monitoring system 100 may include: a total dissolved solids (TDS) sensor and/or an electrical conductivity (EC) Sensor. The processor can obtain measurements from the sensors and then convey this information through transmitters or transceivers. Based upon the measurements and the type of chemical sanitizer being used, the processor 115 can make recommendations for adding chemicals to the water and scheduling chemicals for the water to maintain a proper chemical composition.

Figure 3:
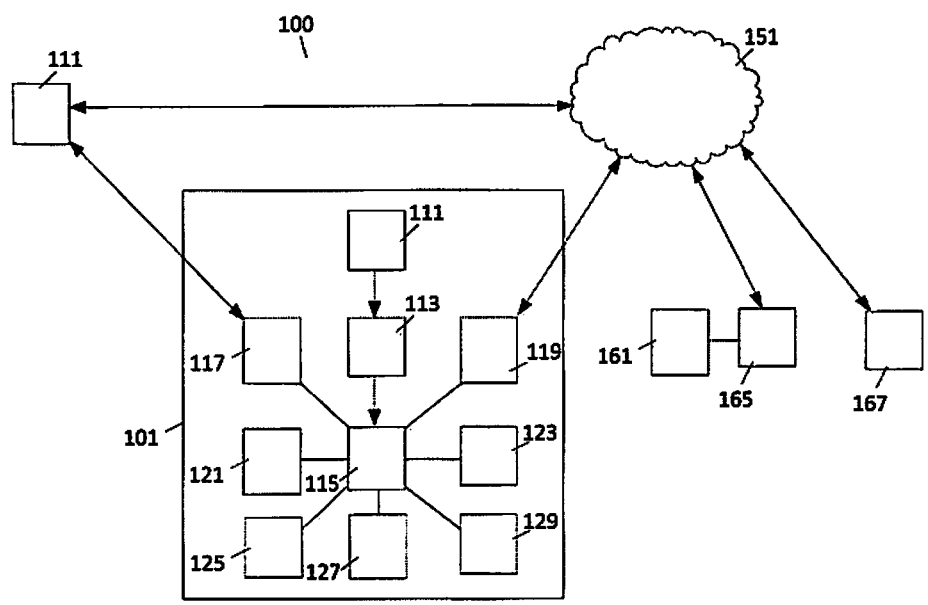
FIG. 3 illustrates a block diagram of an embodiment of the water monitoring unit.

In another embodiment, the device can include hub-spoke type connectivity. With reference to FIG. 3, an example of this would be a hub, such as a Bluetooth and/or WiFi receiver coupled to a computer 111 which can be a smartphone and/or a server 165, that connects via a wireless network 151 to one or multiple water monitoring devices 101 in a pool 102. This hub could then utilize other connectivity methods such as a computer with WiFi, or a cellphone with 3G, to send data to a cloud or other analytics platform. The hub could be self-contained and run the water analytics "in-house." Another device can access the hub and receive information from the hub and analyze data from multiple water monitoring devices. This data can be stored on a computer 111 or server 165 memory and associated with each individual water monitoring device 101. Information for each of the water monitoring devices 101 can be transmitted back to computers 111 associated with each of the water monitoring devices 101. For example, the server 165 may transmit a first message to a mobile phone computer 111 associated with a first water monitoring device 101 that X quantity of chemical A needs to be added to the pool 102 with a note that pools inventory of chemical A is running low. A graphical user interface GUI on the mobile phone computer 111 may include a button asking for authorization to order chemical A from the pool supply store. If the user clicks on the authorization button, the server 165 can transmit a message to a pool supply company 167 to deliver an appropriate quantity of chemical A to the pool 102 associated with the first water monitoring device 101.

In an embodiment, the water monitoring device 101 may include a WiFi or Bluetooth transmitter 117 which can communicate with a local computer 111 which can be a smart phone, computer, server, or other processing device. The water monitoring device 101 may also include a cellular transceiver 119 which can transmit information to a network 111 which can include a cellular network and/or the Internet. In an embodiment, the pool information can be transmitted to a server 165 and the pool information can be stored on a database 161. In an embodiment, the system can be used to run diagnostics on the pool. For example, if a problem is detected the computer 111 or server 165 can request the water monitoring device 101 run chemical testing on demand so that the current chemical measurements can be analyzed. Based upon the cumulative pool results for each region, the system can determine local area chemical optimization. For example, hot and humid areas may require more algaecide and colder and less humid regions. This optimization can result in less need for chemical adjustments and more efficient use of pool chemicals which can result in a lower cost for pool maintenance. The system can also be configured to keep track of the chemicals stored at the pool. If the amount of chemicals in storage runs low, the system can be configured to order additional chemicals from a pool chemical supplier 167.

Figure 5:
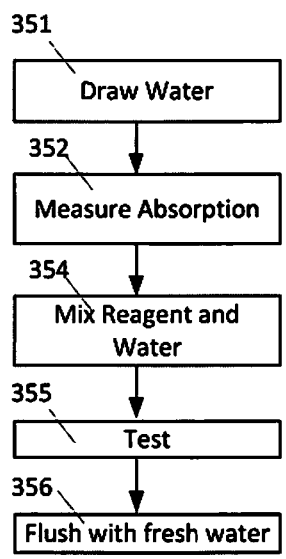
FIG. 5 illustrates a flow chart for an embodiment of pH testing for water.

In an embodiment with reference to FIG. 5, the present invention can comprise of the following components: A device housing 201, which includes an light emitting diode (LED) 213, a photodiode 217 and a cartridge receptacle 211. A cartridge fluidic chip 203 can be inserted into the device housing 201. The cartridge can be a consumable cartridge fluidic chip 203 that houses one or more reagents 205. The cartridge fluidic chip 203 can include pumps 209 and check valves 207 which can pump the reagents 205 into a flowcell 215. The cartridge fluidic chip 203 can also pump pool water from a pool water inlet 219 into the flowcell 215. The reagents 205 can react with the pool water to produce colors based upon the chemical reactions of the reagents 205 and the pool water. The LED 213 can transmit light through the flowcell 215 which can absorb specific wavelengths of light. The light that passes through the flowcell 215 is detected to by the photodiode 217. After the testing has been performed, the system can pump the pool water out of the flowcell 215 through a pool water outlet 221. In addition to the described components, the device housing can also include: a processor 227, a transceiver 225 (or transmitter), a battery 223 power supply which can be charged by a solar cell 331, a memory 229 for storing pool water information and a display 333 for displaying status and water information such as water temperature and/or pH level. When any of the reagents 205 are consumed, the cartridge fluidic chip 203 can be replaced with a new unit that includes full reagents 205.

With reference to FIG. 4, an embodiment of the water monitoring unit 201 can include a replaceable cartridge design. The cartridge fluidic chip 203, can be housed in the receptacle 211 of the water monitoring unit 201. The cartridge fluidic chip 203 can provide: reagent storage 205, pumps 209 for pumping of the reagents into the flow cell 215. The cartridge fluidic chip 203 can also include check valves 207 which can control the movement of the water and reagents through the system. More specifically, reagents from the reagent storage 205 and water from the water inlet 219 are pumped into the flowcell 215 where chemical testing is performed. Once the testing is completed, the water and reagent mixture can be pumped out of the water monitoring unit 201 through the pool water outlet 221. In an embodiment the pumps 209 can be peristaltic, diaphragm, syringe, blister pack or any other suitable chemical pump mechanism. For proper function, the pumps may need to control the fluid volume of 25 uL per pump with an error rate of less than 5%.

The water monitoring unit 201 can include a processor 227, memory 229, a display 333, a battery 223, a transceiver and a solar cell 331. The system components can be powered from electricity from the battery 223 which can be recharged by the solar cell 331 during the day. The processor 227 can be coupled to the memory 229 and control the pumps 209 and the testing performed by the LED 213, flowcell 215 and photodiode 217. The output of the photodiode 217 can be analyzed by the processor 227 to determine the chemicals in the water. The processor 227 can transmit and receive information through the transceiver 225.

In an embodiment, the reagent and water mixed in the proper predefined ratio is tested by exposing the flowcell 215 to one or more LED 213 lights. Specific wavelengths corresponding to specific colors of light will be absorbed by the reagent and water mixture and the photodiode 217 can detect the absorbed wavelengths of light or more specifically, the photodiode 217 will not receive the absorbed wavelengths of light. The output of the photodiode 217 can be transmitted to a processor 227 which can run software which can identify the concentrations of chemicals in the water based upon the absorbed wavelengths of light. In an embodiment, the absorption of light can be based upon a total clear absorption 0-1.0 scale where 1.0 is total absorption. In an embodiment, a calibration absorption test can be run with pure water in the flowcell 215 and the light absorption for plain water can be determined by the photodiode 217. Reagent tests can then be run and the differences in the photodiode 217 output signals can be used to determine the chemicals in the water. In an embodiment, the water monitoring unit 201 may sense 440-635 nm wavelengths of light using the AMS (TAOS) TCS34725 as the photodiode 217.

Once the testing is completed the water and reagents are pumped out of the flowcell 215. The flowcell 215 may then be filled with pool water with a pump 209 to remove any residual reagents prior to the next test. Once any of the reagents or other stored chemicals are depleted, the cartridge fluidic chip 203 can be removed and replaced with a new cartridge fluidic chip 203 that is filled with reagents. In different embodiments, the cartridge fluidic chip 203 may be able to pump and mix a series of fluids including reagents, buffer solutions, and titrants in varying sequences. Although FIG. 4 illustrates all reagent storage 205 as reagents any other necessary chemicals can be stored in the reagent storage 205. The expected life of the cartridge can be about eight months or any other reasonable period of time. At the end of this testing period the cartridge fluidic chip 203 will be replaced by the user.

In an embodiment, the driver pumps 209 can output liquids in 25 uL increments and volume of the flow cell can be approximately 500 uL or any other suitable volume. In an embodiment, the consumable cartridge fluidic chip 203 may accommodate 12 reagents in sufficient volume to allow for 500 tests for approximately 8 months. Note that not the system may perform various types of test each using different reagents on different test schedules. Thus, the cartridge fluidic chip 203 may store different volumes of the reagents based upon the test schedule. The flowcell 215 may have a transparent housing that contains the water and reagents but also allows for optical measurements. In an embodiment, the flowcell 215 can be easily cleaned for accurate and repeatable optical testing. Check valves 207 can prevent the fluids from traveling backwards up the reagent lines.

In different embodiments, different types of driver pumps 209 can be used with the inventive system. For example, in an embodiment the pumps 209 can include a ball and magnet mechanism. The ball can be placed against a membrane and the ball can be moved within a ball chamber with a magnetic field. The magnetic field can cause the magnetic ball to move against the membrane can increase the volume between two of the check valves 207 which can draw fluid into this space through an inlet check value. When the magnetic field is removed, the membrane can compress the volume and force fluid through the outlet check valve 207. In another embodiment, a piston can be placed against a membrane. The movement of the piston can increase or decrease the volume between check valves 207. Expanding the volume can draw fluid into this space through an inlet check value. When the piston is moved in the opposite direction, the membrane can compress the volume and force fluid through the outlet check valve 207. The piston can be controlled with a threaded rotational mechanism which can be rotated to move the piston linearly. The pump can be cycled by rotating the threaded mechanism a specific number and/or partial number of rotations to accurately control the volume of each pump actuation. In other embodiments, any other suitable pump mechanism can be used with the inventive system.

In an embodiment, several different colorimetric tests can be conducted inside the cartridge. Some of the tests need to be tested more often than others. In an embodiment, the system can be configured to automatically run tests according to the schedules in Table 1 below. The volumes are represented by volume/volume percentages (v/v).

TABLE 1

| Test | Test Schedule | Volume v/v | Chemical and function |
|---|---|---|---|
| pH | 2× per day | 4-20% | Phenol Red reagent |
| Free Chlorine | 2× per day | 4-6% | Free Chlorine Phosphate buffer |
| | | 4-6% | Free Chlorine DPD reagent |
| Total Chlorine | 2× per day | 4-6% | Total Chlorine Phosphate buffer |
| | | 4-6% | Total Chlorine DPD reagent |
| Alkalinity 1 | 1× per 7 days | 4-6% | Phenol Red reagent |
| | | ~0.2% increments | 0.12N Sulfuric Acid Titrant |
| Alkalinity 2 | 1× per 7 days | ~0.4% | Sodium Thiosulfate chlorine neutralizer |
| | | 4-6% | bromocresol green-methyl red indicator |
| | | ~0.2% increments | 0.12N Sulfuric Acid Titrant |
| Cyanuric Acid | 1× per 7 days | 45-55% | Melamine reagent |
| Calcium Hardness | 1× per 7 days | ~4% | Calcium Buffer |
| | | ~1% | Calcium Indicator |
| | | ~0.2% increments | Standard EDTA 0.02N Titrant | pH Testing

The testing procedures performed by the water monitoring unit can depend upon the type of testing being performed. For example, with reference to FIG. 5, for pH testing, the water monitoring unit can automatically add the designated reagent to the water 351 in the flowcell. In a preferred embodiment, the volume of water is repeatable with an accuracy of + or −1%. The pool water in the flowcell can then be tested. The water can be by exposed to light from the LED and the transmitted light can be detected by the photodiode. This initial test can determine the light absorption of the pool water prior to adding test chemicals 352. The reagent can then be added to the flowcell and mixed with the water 354. As discussed, the reagent can be phenol red and the volume can be 5% v/v. In other embodiments, any other suitable reagent and volume can be used for testing. The flowcell can include a mixing mechanism such as an agitator which actively mixes the water and reagent. The mixed reagent and water can then be tested 355 for light wavelength absorption. In some embodiments, the total light absorption can be measured and in other embodiments, the light absorption for one or more light wavelength frequencies can be measures. The results of the test can be used to determine the pH level of the pool water. Once testing is complete, the flowcell can be flushed with fresh pool water to remove the reagent from the flowcell 356.

As discussed above, during testing the chemicals mixed with the water can be exposed to light. Some wavelengths of light will be absorbed by the water and the photodiode can be used to measure these absorbed wavelengths. The light absorption test data can be analyzed in different ways depending upon the testing being performed. For example, the pH test can include mixing the reagent phenol red with the water and the absorbed wavelengths are measured with the photodiode. Phenol red exists as a red crystal that is stable in air. Its solubility is 0.77 grams per liter (g/l) in water and 2.9 g/l in ethanol. It is a weak acid with pKa=8.00 at 20° C. (68° F.). A solution of phenol red is used as a pH indicator and the water reagent mixture can exhibit a gradual color transition from yellow to red over the pH range 6.8 to 8.2. Above pH 8.2, phenol red turns a bright pink (fuchsia) color.

Figure 11:
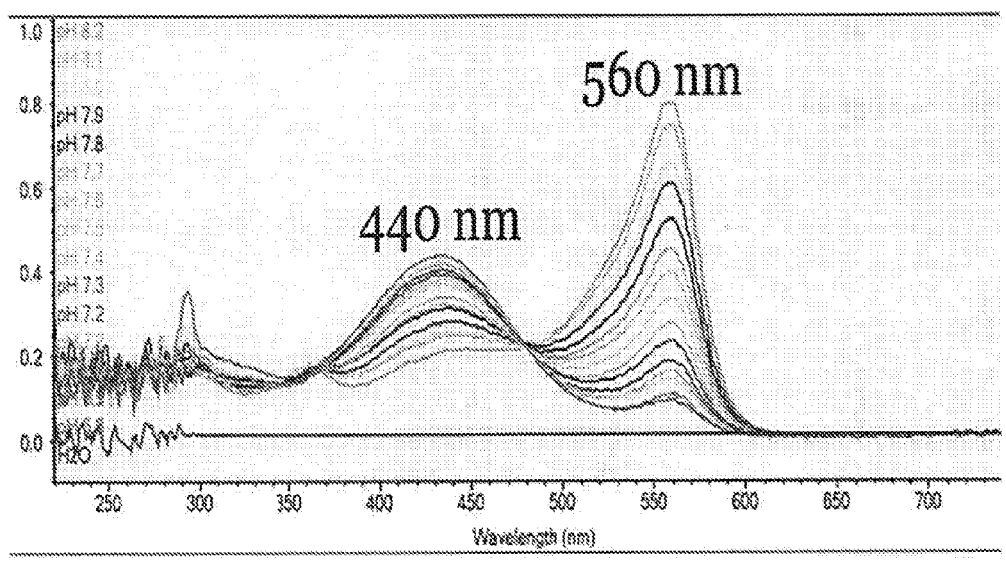
FIG. 11 illustrates a graph for light absorption for different wavelengths of light for phenol red in water.

With reference to FIG. 11 a graph illustrating the light absorption of the water is illustrated. The lower straight lower line 421 between 330 and 700 nm wavelength light can represent the optical absorption of pure water. The curved lines 423 can represent the different light absorptions for different pH levels of water across the 330 and 700 nm wavelength light spectrum. Measuring the absorption at two wavelengths can provide a method for measuring the pH level of the water. In an embodiment, the two wavelengths being measures can be 440 nm and 560 nm and the accurately of the measured pH can be within 5%. At 440 nm the light absorption can be inversely proportional to the pH level of the water being tested. Water having a pH level of about 8.2 can have a 440 nm light absorption of about 0.2 and water having a pH level of about 6.8 can have a 440 nm light absorption of about 0.45. At a 560 nm wavelength the light absorption can be proportional to the pH level of the water being tested. Water having a pH level of 8.2 can have an absorption level of about 0.82 and water having a pH level of 6.8 can have an absorption level of about 0.08 of 560 nm wavelength light.

Figure 12:
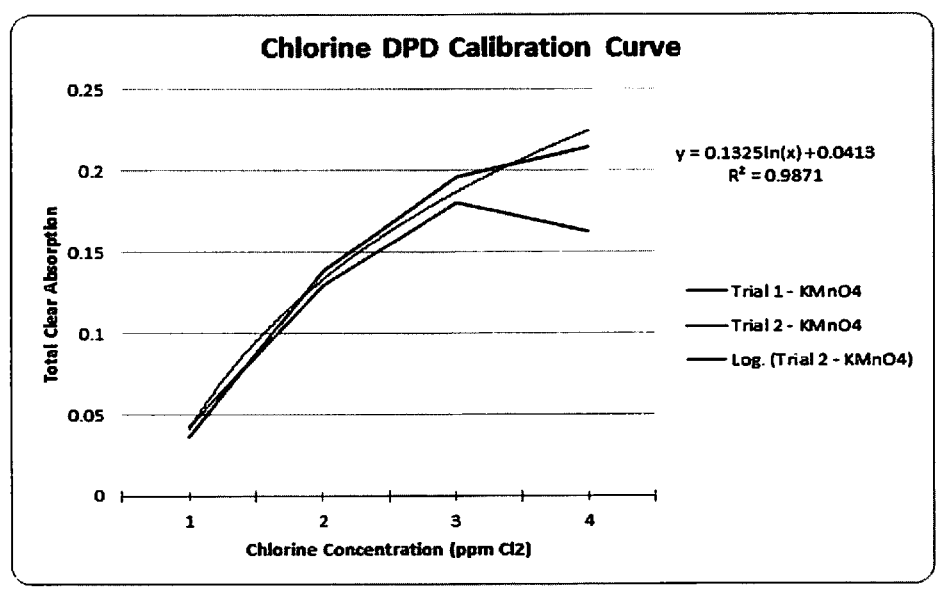
FIG. 12 illustrates a graph for light absorption for chlorine testing.

In an embodiment, the ideal pH level is 7.5 and an acceptable pH level is between 7.4 7.6. With reference to FIG. 12, in an embodiment, the pH level of 7.5 corresponds to an absorption of 0.38 at 440 nm and 0.35 at 560 nm. For pH levels lower than 7.5, the absorption at 440 nm will be higher than 0.38 and the absorption at 560 nm will be lower than 0.35. Conversely, for pH levels higher than 7.5, the absorption at 440 nm will be lower than 0.38 and the absorption at 560 nm will be greater than 0.35. In an embodiment, the pH level for the water can be determined by measuring the absorption ratio (Absorption$_{44\ nm}$/Absorption$_{560\ nm}$) of the 440 nm and 56 nm wavelengths. At a pH of 7.5, the absorption ratio should be 0.38/0.35=1.085. For pH levels below 7.5 the ratio will be less then 1.085 and for pH levels above 7.5 the ratio will be greater than 1.085. As discussed, the pH level of 7.4-7.6 can be acceptable. For a pH level of 7.4, the 440 nm absorption can be about 0.39 and the 560 nm absorption can be about 0.30. For a pH level of 7.6, the 440 nm absorption can be about 0.36 and the 560 nm absorption can be about 0.40. Thus, the 7.4 ratio can be about 0.39/0.30=1.3 and the 7.6 ratio can be about 0.36/0.40=0.9. In an embodiment, the pH level of the water can be determined based upon the detected ratio of the absorption levels at multiple wavelengths of light. This process can allow the water monitoring system to be able to accurately measure pH to within 5% accuracy. Because this process uses ratios rather than specific absorption levels, the system can be less prone to calibration errors of the photodiode sensor. In other embodiments, the light absorption algorithms can be used to determine the pH level of the test water. Although the pH reagent has been described as Phenol Red, in other embodiments, various other reagents can be used to measure the pH level including: azolitmin, bromothymol blue, neutral red, cresol red, naphtholphthalein, and any other suitable reagent.

As discussed, the pool can have an optimum pH level of 7.5 and an acceptable range of 7.4 to 7.6. If the pH level is lower than 7.4, the water monitoring system can recommend adding chemicals such as soda ash to increase the pH level. The quantity of the chemicals added can depend upon the volume of the body of water (pool volume). The recommended chemical adjustment can be based upon an algorithm or a look up table such as Table 2 below which can be stored in the memory of the system. In this example, Table 2 specifies the volume of soda ash to add a pool based upon the pH level and the volume of the pool. Similar algorithms and/or tables can be used to instruct users to lower the pH level by adding a specific volume of an acid such as sodium bisulfate or muriatic acid based upon the pH level and the pool volume. In an embodiment, the system can interpolate the table values to determine the proper volume of chemicals to add. For example, if the pH level is 7.1 and the pool volume is 12,500 gallons, the system can recommend adding 10 oz. of soda ash to correct the pH level.

TABLE 2

| pH Level | 5,000 gallon pool | 10,000 gallon pool | 15,000 gallon pool | 20,000 gallon pool |
|---|---|---|---|---|
| 7.4 | 1.50 oz. | 3.00 oz. | 4.5 oz. | 6.00 oz. |
| 7.3 | 3.00 oz. | 6.00 oz. | 9.00 oz. | 12.00 oz. |
| 7.2 | 3.50 oz. | 7.00 oz. | 10.5 oz. | 14.00 oz. |
| 7.1 | 4.00 oz. | 8.00 oz. | 12.00 oz. | 16.00 oz. |
| 7.0 | 4.66 oz. | 9.33 oz. | 13.33 oz. | 18.66 oz. |
| 6.9 | 5.33 oz. | 10.66 oz. | 14.66 oz. | 21.33 oz. |
| 6.8 | 6.00 oz. | 12.00 oz. | 16.00 oz. | 24.00 oz. |
| 6.7 | 6.66 oz. | 13.33 oz. | 13.33 oz. | 26.66 oz. |
| 6.6 | 7.33 oz. | 14.66 oz. | 22.00 oz. | 29.33 oz. |

Chlorine Testing

Figure 6:
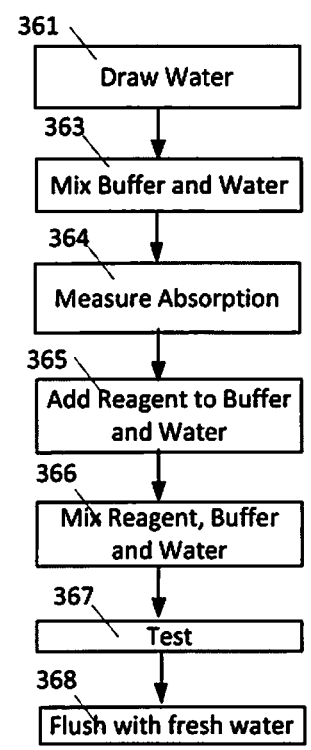
FIG. 6 illustrates a flow chart for an embodiment of chlorine testing for water.

The test procedures for free chlorine are described with reference to FIG. 6. For free chlorine testing, the water may need both a buffer and reagent chemicals. With a test water sample of + or −1%, the free chlorine test can be accurate for + or −0.4 ppm free chlorine. In an embodiment, the monitoring unit can automatically add the designated buffer to the water 361 in the flowcell. The buffer can then be added to the flowcell and mixed with the water 363. In an embodiment, the buffer can be free chlorine phosphate buffer with a volume of 5% v/v. In other embodiments, any other suitable reagent and volume can be used for pH testing. The buffer and water mixture can be tested for base calibration 364 where the buffer and water are exposed to light from the LED and the photodiode detects the transmitted light and determines the absorbed light wavelengths. The reagent can be added and mixed with the buffer and water 365. In an embodiment, the reagent can be free chlorine DPD with a volume of 5% v/v or any other suitable reagent and volume. Testing 367 is then performed to determine the amount of light absorbed by the reacted reagent. In some embodiments, the total light absorption can be measured and in other embodiments, the light absorption for one or more light wavelength frequencies can be measures. Once testing is complete, the flowcell can be flushed with fresh pool water to remove the reagent from the flowcell 368.

Figure 7:
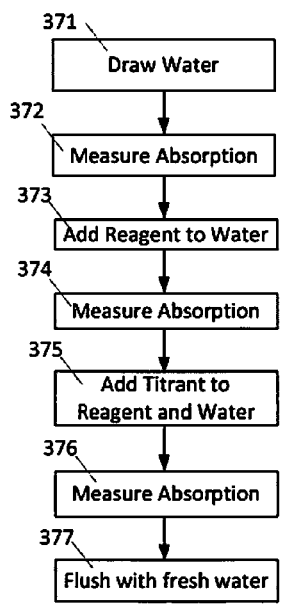
FIG. 7 illustrates a flow chart for an embodiment of alkalinity testing for water.

The test procedures for total chlorine can also be described with reference to FIG. 7. With a test water sample of + or −1%, the total chlorine test can be accurate within + or −0.4 ppm free chlorine. In an embodiment, the monitoring unit can automatically add the designated buffer to the water 361 in the flowcell. The buffer can then be added to the flowcell and mixed with the water 363. In an embodiment, the buffer can be total chlorine phosphate buffer with a volume of 5% v/v or any other suitable reagent and volume can be used for pH testing. The buffer and water mixture can be tested for base calibration 364 where the buffer and water are exposed to light from the LED and the photodiode detects the transmitted light and determines the absorbed light wavelengths. The reagent can be added and mixed with the buffer and water 365. In an embodiment, the reagent can be total chlorine DPD with a volume of 5% v/v or any other suitable reagent and volume. Testing 367 is then performed to determine the amount of light absorbed by the reacted reagent. In some embodiments, the total light absorption can be measured and in other embodiments, the light absorption for one or more light wavelength frequencies can be measures. Once testing is complete, the flowcell can be flushed with fresh pool water to remove the reagent from the flowcell 368.

Figure 13:
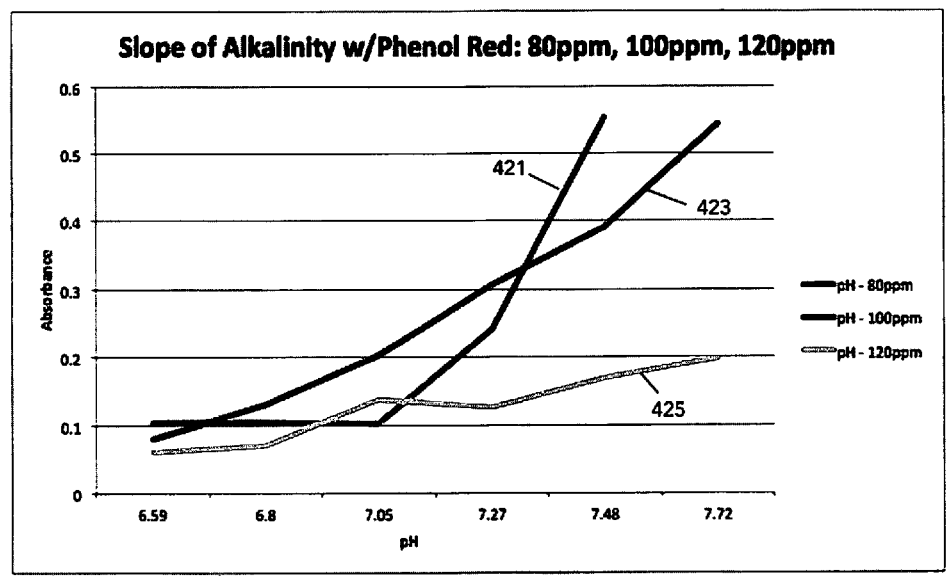
FIG. 13 illustrates a graph of light absorption for alkalinity testing.

As discussed above, the chlorine light absorption testing of water that can be mixed with a buffer and reagent. The chlorine concentration in parts per million (ppm) can be determined by preparing the water for chlorine testing with a buffer as described above. This test will be used to calibrate the absorption values that are being read from the TAOS sensor. The actual testing can be performed by exposing the water with reagent to light and measuring the absorption. FIG. 13 illustrates an embodiment of a graph showing a relationship between total clear light absorption and the chlorine concentration of the water. If the chlorine optical test results have a light absorption of about 0.1, the chlorine concentration can be about 1.6 ppm $CL_2$ which can be within the target value of 1.0 to 3.0 ppm. In an embodiment the graph illustrated in FIG. 13 can be represented by the equation Absorption=0.1325 ln ($Cl_2$ concentration)+ 0.0413. By knowing the absorption, this equation can be used to solve the $Cl_2$ level. The graph can have an R2 value of 0.98 for a curve fit of chlorine between the ranges of 1-4 ppm.

In an embodiment, it can be desirable to maintain a pool with a chlorine level of about 1.0-3.0 ppm. If the pool water has a lower than ideal chlorine level the system can suggest adding chlorine to the pool based upon the desired increase in chlorine levels and the volume of the pool. Similar algorithms can be used to calculate the quantities of chemicals needed to reduce the chlorine level of the pool.

The chlorine test chemicals can have specific characteristics which can be important for accurate test results. More specifically, DPD chemistry can distinguish the active sanitizer, termed free available chlorine. When DPD in either liquid form is added to a water sample, a pink color forms with an intensity proportional to the chlorine concentration (either free or total, depending on the step of the procedure). The color of the treated sample is then compared to a set of color standards.

Subtracting the free chlorine reading from the total chlorine reading can yield the amount of combined chlorine in the water. Combined chlorine, an ineffective sanitizer, causes eye and mucous membrane irritation and the so-called "chlorine odor" associated with poorly maintained pools. Combined chlorine is eliminated by super-chlorinating to the breakpoint dosage. Calculations for breakpoint dosage can depend on knowing the amount of combined chlorine in the water, which is why DPD is superior to OT for testing chlorine-sanitized pools.

Without the chlorine phosphate buffer the DPD fades away. When the DPD is oxidized there are two competing products, one is colorless and the other, colored. The colorless can be the preferred product in the solution, thus the phosphate buffer assists in leaving the colored product 20×-30× in time. Also, the slightly acidic pH can be preferred to resolve the chloramine species quantitatively and to minimize interferences.

Alkalinity Testing

An embodiment of alkalinity testing can also be described with reference to FIG. 7 using a two point test method which can include pH level and light absorption data. With a test water and test chemical sample of + or −1%, the alkalinity test can be accurate within + or −20 ppm $CaCO_3$. The system can fill the flowcell with pool water 371. The system can measure the light absorption of the pool water as a sample blank 372. The system can then mix a reagent with the water 373. In an embodiment, the reagent can be phenol red mixed with a 4-6% v/v volume. In other embodiments any other suitable reagent and volume can be used. The reagent and water can be light absorption tested 374 which is a first data point which can be the pH level. A titrant can then be added to the water and reagent 375. In an embodiment the titrant can be 0.012N sulfuric acid added in 0.2% increments. Light absorption testing can be performed 276. The addition of titrant step 375 and measuring steps 376 can be repeated until the end point is determined. In some embodiments, the total light absorption can be measured and in other embodiments, the light absorption for one or more light wavelength frequencies can be measures. Once testing is complete, the flowcell can be flushed with fresh pool water to remove the reagent from the flowcell 377.

Figure 8:
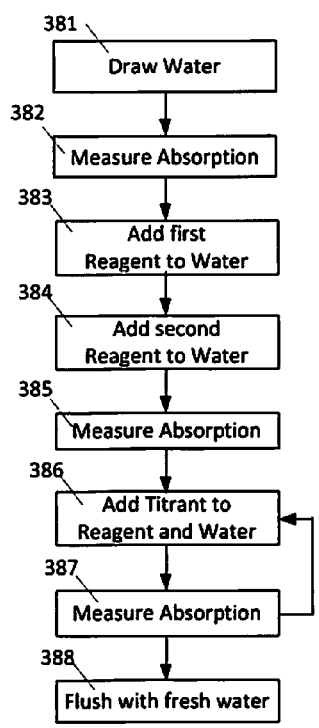
FIG. 8 illustrates a flow chart for an embodiment of alkalinity testing for water.

In other embodiments, the alkalinity of the pool water can be tested using a full titration method with reference to FIG. 8 using a full titration method. Fresh pool water is drawn into the flow cell 381 and the system can measure the light absorption of the pool water as a sample blank 382. The system can then mix a plurality of reagents with the water. A first reagent can be added to the water 373. In an embodiment, the first reagent can be sodium thiosulfate which is a chlorine neutralizer mixed with a 0.4% v/v volume. A second reagent can then be added to the water 384. In an embodiment, the second reagent can be bromocresol green-methyl red indicator which can be mixed with a 4-6% v/v volume. In other embodiments any other suitable first and/or second reagents and volumes can be used. The water with first and second reagents can be measured for light absorption 385. A titrant can then be added to the water and reagents 386. In an embodiment, the titrant can be a 0.12N sulfuric acid titrant which can be added with 0.2% v/v volume increments 386. The water with titrant can be measured for light absorption 387. The titrant adding step 386 and the optical measuring step 387 can be repeated until an endpoint is reached. In some embodiments, the total light absorption can be measured and in other embodiments, the light absorption for one or more light wavelength frequencies can be measures. Once testing is completed, the flowcell can be flushed with fresh pool water 388.

Alkalinity can be measured using phenol red as well as a sulfuric acid buffer. With reference to FIG. 13, an embodiment of a graph that shows a relationship between light absorption and pH change. Sulfuric acid can be used as a titrant to estimate the alkalinity. For example, the three lines on the graph represent different alkalinities of 80 ppm (421), 100 ppm (423), and 120 ppm (425). By knowing the absorption and the pH change, the alkalinity can be estimated. For example, if the absorption is 0.1 and the pH change is 7.05, then the alkalinity corresponds to the line 421 and the alkalinity is about 80 ppm.

Total alkalinity is a measure of the total amount of dissolved particles in the water whose pH is higher than 7.0. Total Alkalinity (TA) should usually be kept at 80-120 ppm. If the measurement data does not correspond to the graphed lines, this can indicate that the total alkalinity can be outside the normal desired range. If the TA is too low, Marbelite and plaster walls can become etched, metals corrode, the pool's walls and floor can stain, the water can turn green, eyes burn and we can have pH bounce (pH rapidly going up and down, seemingly at random). To raise the level of TA, the system can recommend adding a specific quantity of sodium bicarbonate which can increase the TA without increasing the pH significantly. The system may recommend only adding sodium bicarbonate at the rate of 1 kg per 50,000 liters of water every 4 days. If the TA is too high, the water can become cloudy, the pool may constantly need acid (according to your test kit) and the chlorine loses its efficiency as a disinfectant. To lower the TA, the system can recommend adding acid to the pool at a specific slow rate.

Figure 14:
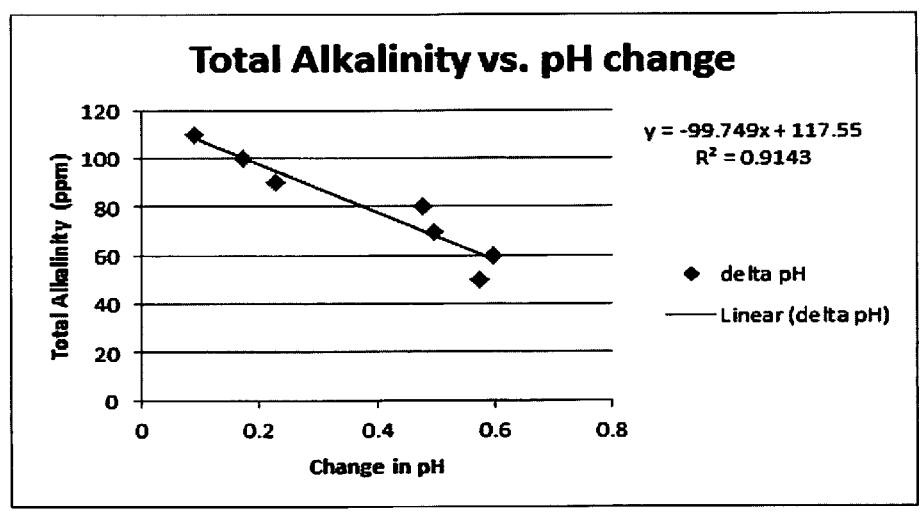
FIG. 14 illustrates a graph of alkalinity for a change in pH.

In another embodiment, the total alkalinity can be determined based upon the change in pH. As discussed, the change in pH can indicate a lower than normal TA. FIG. 14 illustrates an embodiment of a graph representing the relationship between the TA and the change in pH. For example, if the pH changes by 0.6, this can indicate that the pool has a TA of about 50-60 ppm.

Cyanuric Acid Testing

Figure 9:
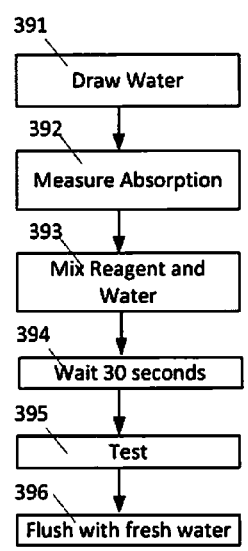
FIG. 9 illustrates a flow chart for an embodiment of cyanuric acid testing for water.

An embodiment of cyanuric acid testing is described with reference to FIG. 9. With a test water and test chemical sample of + or −5% volume accuracy, the cyanuric acid test can be accurate within + or −11 ppm CYA. For cyanuric acid testing, water is drawn into the flowcell 391. The pool water is exposed to light and measured for light absorption 392. A reagent is added and mixed with the water in the flowcell 393. In an embodiment, the reagent can be a melamine solution which is added at 50% v/v. In other embodiments any other suitable reagent and volume can be used. The reagent and water can mix for 30 seconds 394. The reagent and water can be light tested and the results can be analyzed for absorption 395. In some embodiments, the total light absorption can be measured and in other embodiments, the light absorption for one or more light wavelength frequencies can be measures. Once testing is completed, the flowcell can be flushed with fresh pool water 396.

Figure 15:
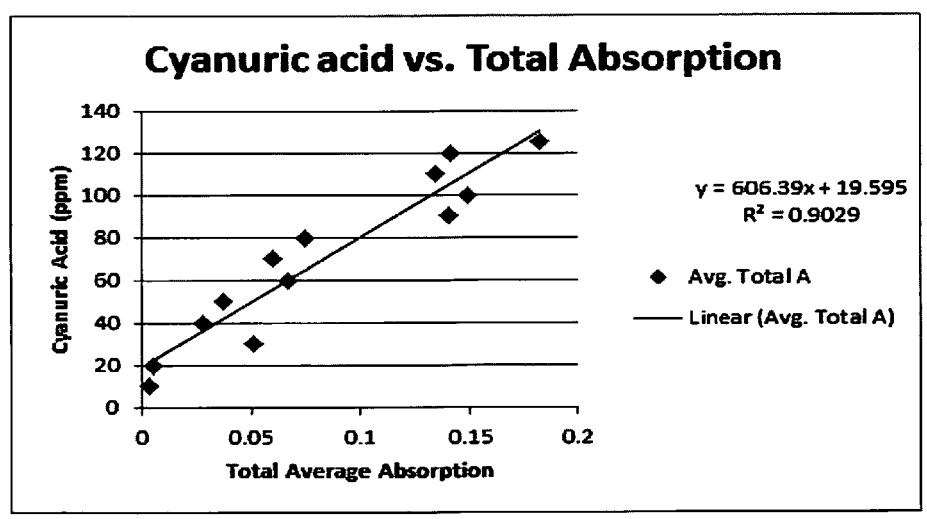
FIG. 15 illustrates a graph of light absorption for cyanuric acid testing.

With reference to FIG. 15, a graph is illustrated that shows a graphical relationship between the light absorption and the cyanuric acid levels. If the light absorption of the pool water is about 0.05 then the cyanuric acid level can be about 50 ppm. In an embodiment, this relationship can be represented by the algorithm cyanuric acid (ppm)=606.39 (total average light absorption)+19.595. In other embodiments, any other accurate graphs and/or algorithms can be used to convert the light absorption to cyanuric acid level. The ideal cyanuric acid level can depend upon various environmental factors including chlorine loss rate, temperature, sun exposures, etc. When an ideal cyanuric acid level is determined, the system can recommend the addition of chemicals to the pool to correct the cyanuric acid level based upon the volume of the pool.

The cyanuric acid test chemicals can have specific characteristics which can be important for accurate test results. The cyanuric acid test is a precipitation measurement, which uses melamine and other buffers to precipitate out the melamine into melaminecyanurate. The graph in FIG. 15 shows at different cyanuric acid ppm concentrations at different total average absorption levels. Testing for cyanuric acid concentration is commonly done with a turbidimetric test, which uses a reagent, melamine, to precipitate the cyanuric acid. The relative turbidity of the reacted sample quantifies the CYA concentration. This test works because melamine combines with the cyanuric acid in the water to form a fine, insoluble, white precipitate (melamine cyanurate) that causes the water to cloud in proportion to the amount of cyanuric acid in it.

Calcium Hardness Testing

Figure 10:
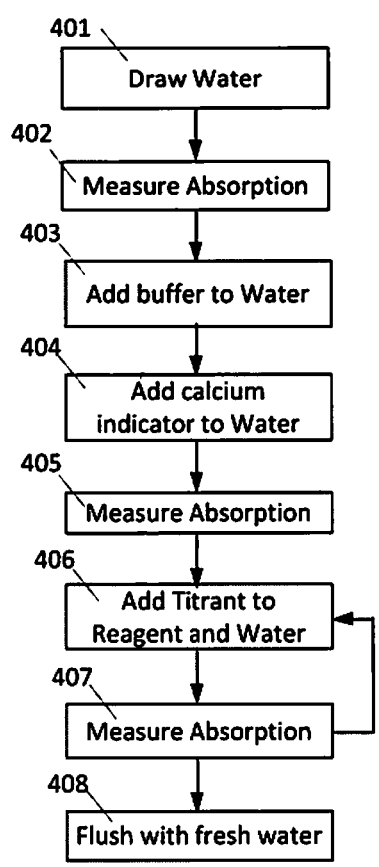
FIG. 10 illustrates a flow chart for an embodiment of calcium hardness testing for water.

For calcium hardness testing a different procedure may be necessary. With reference to FIG. 10 an embodiment of a calcium hardness test is described. Water is drawn into the flowcell 401. The pool water is exposed to light and measured for light absorption 402. A buffer is added and mixed with the water 403. In an embodiment the buffer can be a calcium buffer such as NaOH buffer that has a 4% v/v volume. A calcium indicator can then be added to the water 404. In an embodiment, the calcium indicator can be added at 1% v/v volume. The water can then be tested to measure light absorption 405. A titrant can then be added to the water 406. In an embodiment the titrant can be EDTA 0.02 N titrant which is added at 0.2% v/v increments. The water with buffer, calcium indicator and titrant can then be tested for light absorption 407. The titrant adding step 406 and the test step 407 can be repeated until the endpoint is reached and the calcium hardness can be determined from the test results. Once the testing is completed, the flowcell can be flushed with fresh pool water 408.

Figure 16:
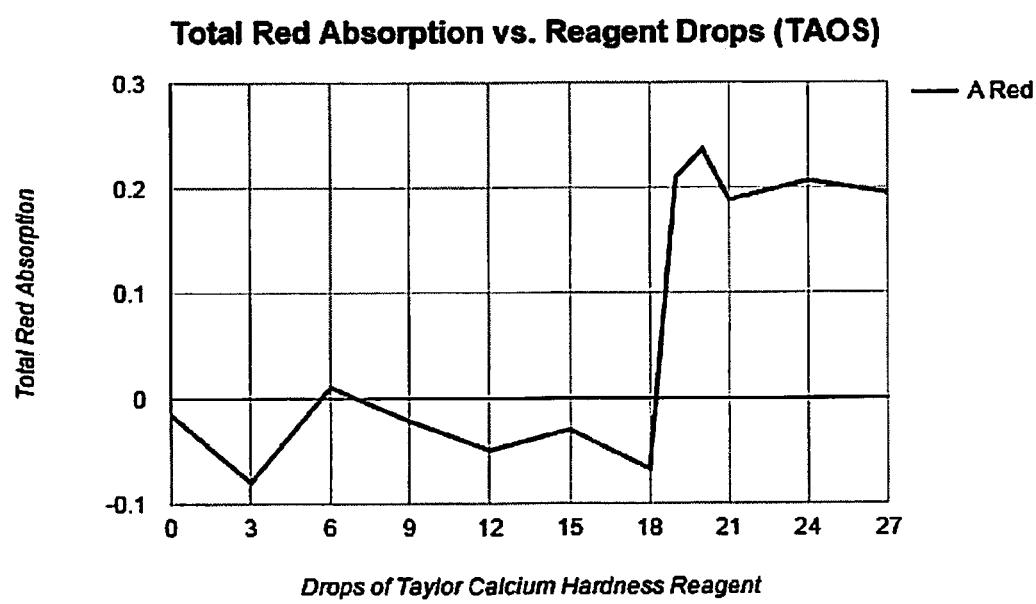
FIG. 16 illustrates a graph of light absorption for calcium hardness testing.

FIG. 16 illustrates a graph of calcium hardness which is measured via an inflection point which results in a large change in the total red absorption. In this example, the inflection points occurs at 19 drops of a Taylor calcium hardness reagent. The volume of reagent needed to reach the inflection point indicates the calcium hardness of the water. In an embodiment, there can be a direct correlation between the number of drops to the inflection point and the calcium hardness. For example, the calcium hardness can be determined by multiplying the number of drops to the inflection point by 10. So in this example, the calcium hardness can be 190 ppm. The ideal calcium hardness can be about 200-400 ppm for pools and 150-250 ppm for spas. In some embodiments, the optimum calcium hardness can depend upon the pool materials for example, the ideal calcium hardnesses can be: 200-400 ppm for plaster pools, 80-150 ppm for vinyl pools and 150-250 ppm for fiberglass pools.

Once the measured calcium hardness is determined, the system can recommend adding chemicals if adjustments are necessary. For example, to increase the calcium hardness the system can recommend adding calcium chloride ($CaCl_2$). The quantity of calcium chloride recommended by the system can be proportional the change in calcium chloride level desired and the volume of the body of water, pool or spa.

The calcium hardness test chemicals can have specific characteristics which can be important for accurate test results. EDTA 0.02 N titrant—Disodium dihydrogen ethylenediamine-tetraacetate ($Na_2EDTA$) forms a slightly ionized, colorless, stable complex with alkaline earth ions. The indicator Eriochrome Black T is bright blue in the absence of alkaline earths, but with them forms a deep-red complex that has a higher ionization constant than that of the $Na_2EDTA$ complex. Hence, with Eriochrome Black T as an indicator, the alkaline earth can be titrated with $Na_2EDTA$.

NaOH buffer—ASDAll alkaline earths titrate approximately stoichiometrically. The titration should proceed immediately upon addition of the indicator, because the color of the solution fades after standing. The optimum pH of the titration is 10.4 or above. The NaOH buffer achieves this pH for the titration.

Calcium indicator—The indicator Eriochrome Black T is bright blue in the absence of alkaline earths, but with alkaline earths this indicator forms a deep-red complex that has a higher ionization constant than that of the $Na_2EDTA$ complex. Hence, with Eriochrome Black T as an indicator, the alkaline earth can be titrated with $Na_2EDTA$.

System Operations

Figure 17:
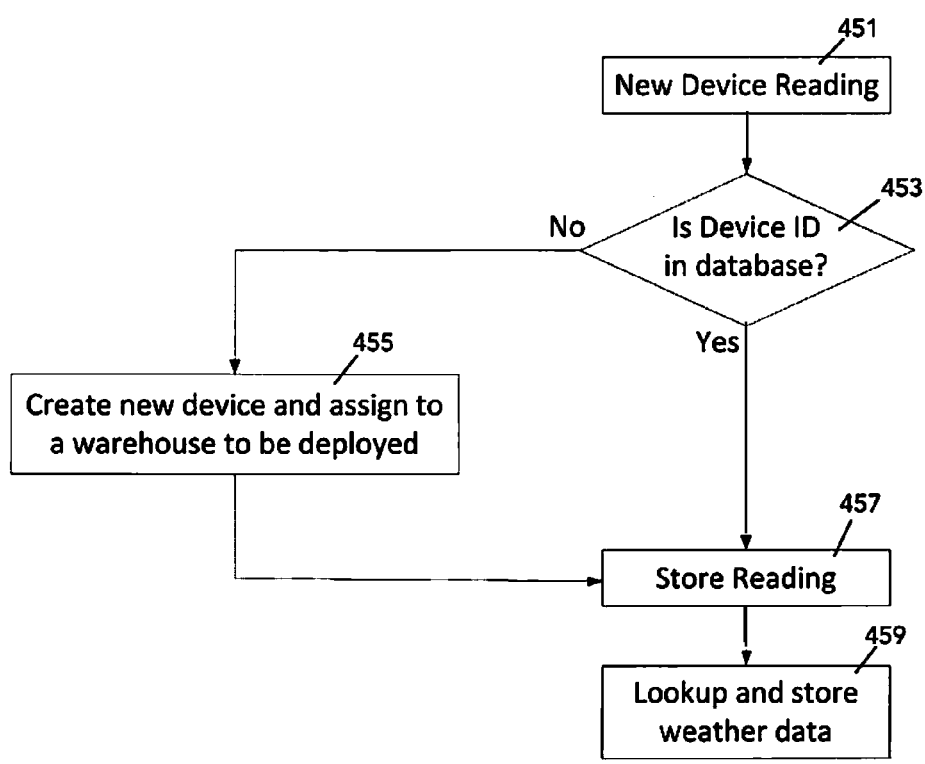
FIGS. 17 and 18 illustrate flow charts for setting up water monitoring systems.

In an embodiment, the system can require an initial set up process after the water monitoring device is purchased. With reference to FIG. 17, an embodiment of the system set up process is illustrated. The water monitoring device can be coupled to a home network and the user can down load a water monitoring application program to a computing device such as a smart phone that can run a set up process. The application can read identification information for the new water monitoring device 451 and the identification information can be transmitted through a network to a water monitoring server to determine if the device is in a database. If the device is new, it will not be in the database. The server will inform the computing device that the device is not in the database and the server will create a new record for the new device and associated information such as location, pool information, chemical information, local warehouse for chemicals, etc. 455. The device and associated information can be then be stored in the server and/or local computing device database. Based upon the location of the pool, the system can lookup and store current and future predicted weather data 459. The current and upcoming weather can be used to predict chemical use. For example, hotter temperatures and sun exposure will result in a loss of chlorine. In an embodiment, the inventive system can factor in the thermal and solar exposure of the pool based upon the weather and season of the year. The system can increase the predicted consumption of chlorine based upon elevated temperatures and increased sun exposure or conversely reduce the predicted consumption of chlorine based upon lower temperatures and decreased sun exposure.

Figure 18:
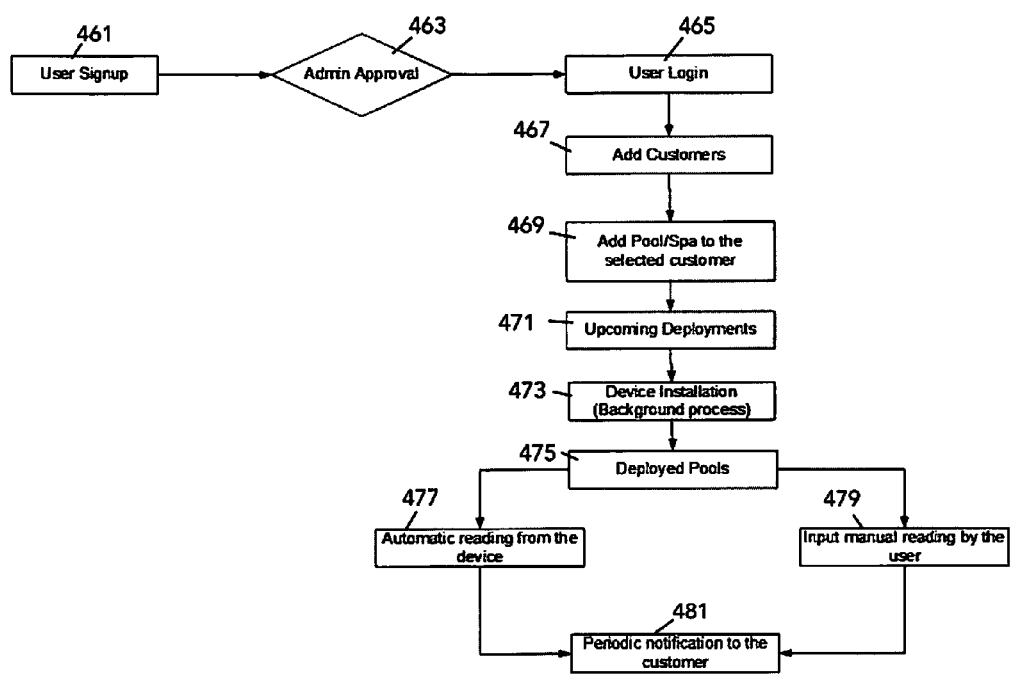

With reference to FIG. 18, another embodiment of a flowchart for setting up a water monitoring system is illustrated. An application program can be used by a new user to input signup information 461 into a computing device. The signup request can be transmitted to a server and a system administrator can accept or reject the new user 463. If the user is accepted, the system can provide secure (such as password protected) user login information. The user can then login to the server 465. The server can add the new customer to the user database 467. The user can input pool or spa information through a user interface and this information can be added to the database and can be associated with the customer 469. The user can configure the system to function in the desired manner such as selecting automated and/or manual pool measurements, chemical notifications and/or deliveries, automated or manual software updates, etc. Based upon the user and pool information, the system can determine upcoming deployments 471 of pool chemicals. The system can then run through a water monitoring device installation process 473. In an embodiment, this device installation process can run in the background automatically through the computing device and the water monitoring device. The installation can include updates to software and/or firmware. Once setup, the device can be deployed to the pool 475. The system can be configured to perform automatic readings from the water monitoring device 477 or perform pool readings based upon manual inputs to the computing device 479. The monitoring information from the pool can be transmitted to the computing device and/or server. Based upon the water monitoring information, the server and/or computing device can provide periodic notifications to the customer user regarding the status of the pool.

In different embodiments, the user's computing device includes a receiver that receives and stores a set of values in the water monitoring database. The data fields that this controller currently receives and processes including information for: battery, water and air temperature, light, pH level, chlorine level, alkalinity, cyanuric acid level and calcium hardness. A Python script has been developed to simulate the device updates. This script can send static data to the water monitoring application program running on the computing device through an API call. For example, in an embodiment, a weather API can be called every time a reading is obtained from a water monitoring device. This call can be originated in the receiver and can change and be limited to a rate of not more than one call per hour. In an embodiment, the weather API can fetch one or more weather details such as: temperature, relative humidity, ultraviolet (UV) and wind speed based on the zip code of the pool's/ spa's location. This information can be used to update the user pool database and can be applied to other pool databases in the area.

Based upon the pool monitoring information, that is transmitted to the user's computer, various messages can be given to the pool maintenance person. More specifically, the user flows can include the following: 1. Everything is good with the users pool (or spa). 2. The user needs to reboot device as there are some issues with connectivity, 3. The user needs to put some chemicals in their pool and 4. The user needs to refill chemicals in storage.

If everything is good the user computing device can display a user interface which indicates that all is good and no action is required. The user interface may display information regarding the actual pool chemical measurements and temperature.

If the system need to be rebooted, the user interface can display a reboot control button which the user can press to actuate the reboot procedure. The system can restart the software application and hopefully reestablish connectivity between the system components. If the system is successful, the system will display "everything is good" on the user interface. If connectivity problems persist, the user interface may ask the user to check the power supply and/or network functionality to determine if the network is down.

If pool chemicals are needed, the system can provide instructions on which chemicals should be added to the pool and the quantity of the chemicals that need to be added. In an embodiment, the inventive system can communicate with a pool maintenance service which can be instructed to put the required chemicals in the pool. The water monitoring device can retest the water and if the pool chemicals and measurements are at the desired levels, the system can display "everything is good" on the user interface.

In an embodiment, the system can monitor the chemicals in storage as well as the chemicals consumed by the pool as instructed by the system. When a supply of chemicals is running low, the system can inform the pool maintenance person. In an embodiment, the user interface can include a button that can be pressed by the user to order the needed chemicals. The system can provide the cost for the chemicals and delivery/tax costs. If the user agrees to the sale price, the system can electronically order the necessary chemicals which can be picked up or delivered to the pool.

The present disclosure, in various embodiments, includes components, methods, processes, systems and/or apparatus substantially as depicted and described herein, including various embodiments, sub-combinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

What is claimed is:

1. A water monitoring system comprising:
a water monitoring device comprising:
a cartridge fluidic chip having: phenol red, a light source, a flowcell for mixing the phenol red and water, a light sensor for detecting light from the light source that is transmitted through fluids placed in the flowcell;
a processor coupled to the light sensor for analyzing light data from the light sensor and determining a pH level of the water;
a transmitter coupled to the processor for transmitting the pH level of the water;
a battery for storing electrical energy and powering the processor, light source, light sensor and transmitter; and
a housing surrounding the processor, the cartridge fluidic chip, transmitter and battery;
wherein the light sensor detects the transmitted light through the phenol red and the water in the flowcell at a first wavelength and a second wavelength that has a longer length than the first wavelength and the pH level of the water is determined by the processor based upon a ratio of the transmitted light at the first wavelength divided by the transmitted light at the second wavelength and wherein when the ratio is greater than 1.3 the water monitoring system recommends adding chemicals to the water.

2. The water monitoring system of claim 1 wherein the water monitoring device further comprises a solar panel for charging the battery.

3. The water monitoring device of claim 1 wherein the water monitoring device further comprises a GPS sensor coupled to the processor for determining a location of the water monitoring device and location information is transmitted by the transmitter.

4. The water monitoring system of claim 1, wherein the pH level of the water is transmitted to a mobile computing device running a water monitoring application program that includes a user interface which displays the pH level of a pool.

5. The water monitoring system of claim 4, wherein the user interface of the water monitoring application program displays a quantity of soda ash to increase the pH level of the water based upon the current pH level and the volume of the pool.

6. The water monitoring system of claim 4, wherein the user interface of the water monitoring application program displays a quantity of acid to decrease the pH level of the water based upon the current pH level and the volume of the pool.

7. The water monitoring system of claim 1, wherein the water monitoring device is used to determine at least one of the following water characteristics: free chlorine level, total chlorine level, alkalinity level, cyanuric acid level, and calcium hardness.

8. The water monitoring system of claim 1, wherein the water monitoring device further comprises, check valves and pumps for moving water and reagents into the flowcell.

9. The water monitoring system of claim 1, wherein the cartridge fluidic chip includes at least one of the following: a free chlorine phosphate buffer for free chlorine testing, a free chlorine DPD reagent for free chlorine testing, a total chlorine phosphate buffer for total chlorine testing, a total chlorine DPD reagent, a sulfuric acid titrant for alkalinity testing, a sodium thiosulfate chlorine neutralizer bromocresol green-methyl red indicator for alkalinity testing, a melamine reagent for cyanuric acid testing, a calcium buffer for calcium hardness testing, a calcium indicator for calcium hardness testing, and a EDTA titrant for calcium hardness testing.

10. A water monitoring system comprising:
a water monitoring device comprising:
- a cartridge fluidic chip having: a phenol red reagent, a light source, a flowcell for mixing the phenol red reagent and water, a light sensor for detecting light from the light source that is transmitted through the water and the phenol red reagent placed in the flowcell;
- a processor coupled to the light sensor for analyzing the light from the light sensor and determining a pH level of the water;
- a transmitter coupled to the processor for transmitting the pH level of the water;
- a battery for storing electrical energy and powering the processor, light source, light sensor and transmitter; and
- a housing surrounding the processor, the cartridge fluidic chip, transmitter and battery;

a mobile computing device coupled to a network, the mobile computing device running a water monitoring application program that includes a user interface which displays the pH level of a pool; and a server coupled to the network, the server receiving pool information from the mobile computing device and/or the water monitoring device and storing the pool information including pH level, pool temperature and pool volume on a pool database;

wherein the light sensor detects the transmitted light through the phenol red reagent and the water in the flowcell at a first wavelength and a second wavelength that has a longer length than the first wavelength and the pH level of the water is determined by the processor based upon a ratio of the transmitted light at the first wavelength divided by the transmitted light at the second wavelength and wherein when the ratio is greater than 1.3 the water monitoring system recommends adding chemicals to the water.

11. The water monitoring device of claim 10 wherein the water monitoring device further comprises a GPS sensor coupled to the processor for determining a location of the water monitoring device and location information is transmitted by the transmitter to the server.

12. The water monitoring device of claim 11 wherein the server receives weather information for the location of the water monitoring device and transmits the weather information to the mobile computing device.

13. The water monitoring system of claim 12, wherein the user interface of the water monitoring application program displays a quantity of soda ash to increase the pH level of the water based upon the current pH level and the volume of the pool and wherein the quantity of soda ash is adjusted based upon the weather information.

14. The water monitoring system of claim 12, wherein the user interface of the water monitoring application program displays a quantity of acid to decrease the pH level of the water based upon the current pH level and the volume of the pool and wherein the quantity of acid is adjusted based upon the weather information.

15. The water monitoring system of claim 10, wherein the first wavelength is 440 nm and the second wavelength is 560 nm.

16. The water monitoring system of claim 10, wherein a first light absorption at the first wavelength divided by a second light absorption at the second wavelength is an absorption ratio that is between 0.9 and 1.3.

17. The water monitoring system of claim 10, wherein the light sensor detects the transmitted light at two wavelengths and the pH level of the water is determined by the processor based upon a ratio of the transmitted light of the two wavelengths.

18. The water monitoring system of claim 10, wherein the light sensor detects light from the light source that is transmitted through the water in the flowcell before the phenol red reagent is placed in the flowcell and after the phenol red reagent is placed in the flowcell.

* * * * *